US00PP30863P2

(12) United States Plant Patent
Kaneppele

(10) Patent No.: US PP30,863 P2
(45) Date of Patent: Sep. 3, 2019

(54) APPLE TREE NAMED 'FENGAPI'

(50) Latin Name: *Malus domestica (Borkh.)*
Varietal Denomination: Fengapi

(71) Applicant: Feno GmbH, Neumarkt (BZ) (IT)

(72) Inventor: Reinhard Kaneppele, Termeno S.S.D.V. (IT)

(73) Assignee: Feno GmbH, Neumarkt (BZ) (IT)

( * ) Notice: Subject to any disclaimer, the term of this patent is extended or adjusted under 35 U.S.C. 154(b) by 0 days.

(21) Appl. No.: 15/932,456

(22) Filed: Feb. 28, 2018

(51) Int. Cl.
*A01H 5/08* (2018.01)
*A01H 6/74* (2018.01)

(52) U.S. Cl.
USPC ..... Plt./161

(58) Field of Classification Search
None
See application file for complete search history.

(56) References Cited

PUBLICATIONS

UPOV-PLUTO: Plant Variety Database—Feb. 2, 2019; cultivar name 'Fengapi' (1 page total).*

* cited by examiner

*Primary Examiner* — Susan McCormick Ewoldt
(74) *Attorney, Agent, or Firm* — The Webb Law Firm

(57) ABSTRACT

A new and distinct *Malus domestica* (Borkh.) variety is provided that produces apples having a vivid red fruit skin color and good eating qualities.

4 Drawing Sheets

Botanical classification: *Malus domestica* (Borkh.)
Varietal denomination: 'Fengapi'.

BACKGROUND OF THE INVENTION

The present invention comprises a new and distinct variety of apple tree, botanically known as *Malus domestica* (Borkh.), and referred to by the varietal name 'Fengapi'. The new variety was discovered in 2002 in Codevigo, Italy. The new variety is the result of a planned breeding program with the purpose of developing new apple tree varieties in which *Malus domestica* (Borkh.) 'Gala' (female parent, U.S. Plant Pat. No. 3,637) was crossed with *Malus domestica* (Borkh.) 'Pink Rose' (male parent, unpatented). 'Fengapi' was asexually reproduced by chip-budding in Codevigo, Italy. The new variety exhibits similar fruit skin color to its female parent, but has a later harvest time and differs in fruit shape. 'Fengapi' has an earlier harvest time than its male parent. When compared to both parental varieties, 'Fengapi' differs in taste and shelf life. 'Fengapi' has very good eating qualities with a crunchy flesh texture like *Malus domestica* (Borkh.) 'Gala 0502' (U.S. Plant Pat. No. 28,235). However, the fruit skin color of 'Fengapi' is vivid red (46C) and the fruit skin color of 'Gala 0502' is deep red-purple (59A). Further, 'Fengapi's harvest time, vigor, fruit skin color, taste, shelf life, and fruit shape distinguish this new variety from other *Malus domestica* (Borkh.) varieties known to the inventor.

The new variety has been trial and field tested and has been found to retain its distinctive characteristics and remain true to type through successive propagations.

DESCRIPTION OF THE DRAWINGS

The accompanying photographic drawings illustrate the new cultivar at approximately 3 years of age, with the color being as nearly true as is possible with color illustrations of this type.

DESCRIPTION OF THE PLANT

Figure 1:
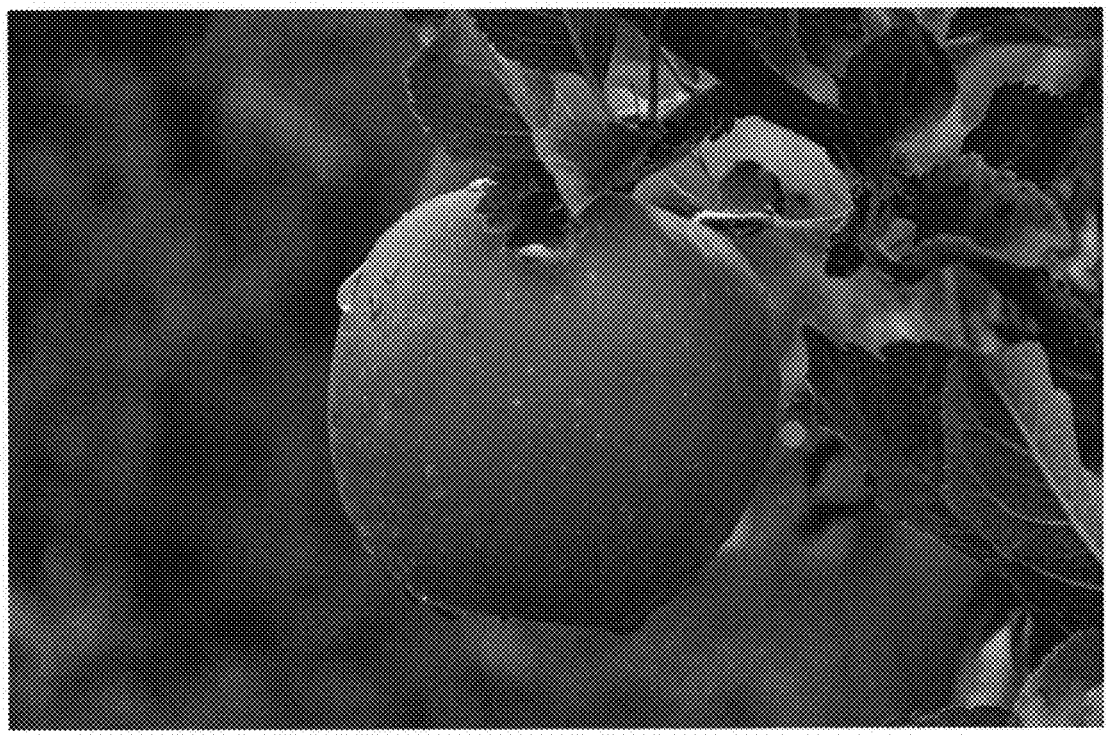
FIG. 1 is a close-up view of a fruit of the new variety at maturity on the tree.
Figure 2:
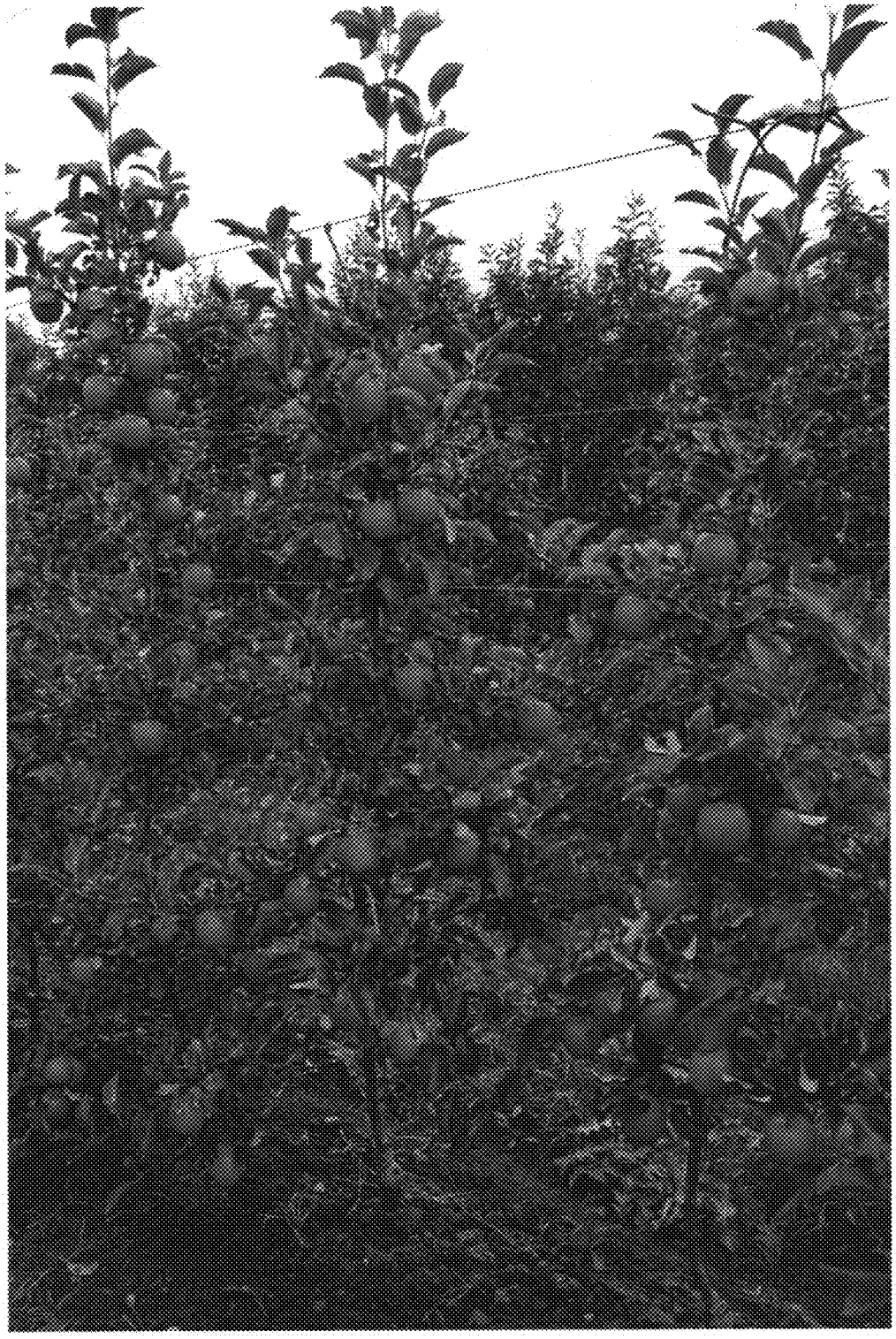
FIG. 2 shows multiple trees of the new variety.
Figure 3:
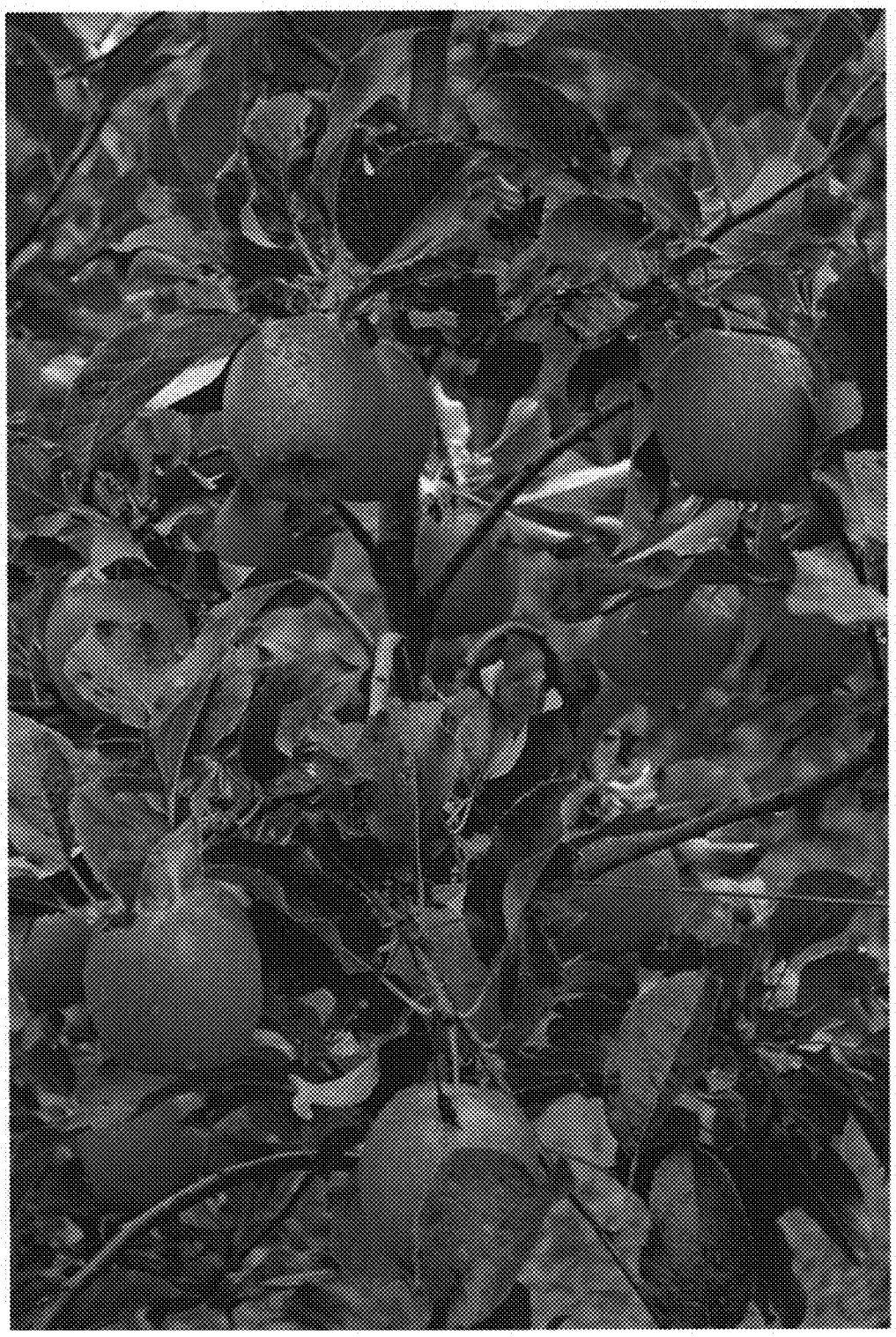
FIG. 3 shows fruits of the new variety at maturity on the tree.
Figure 4:
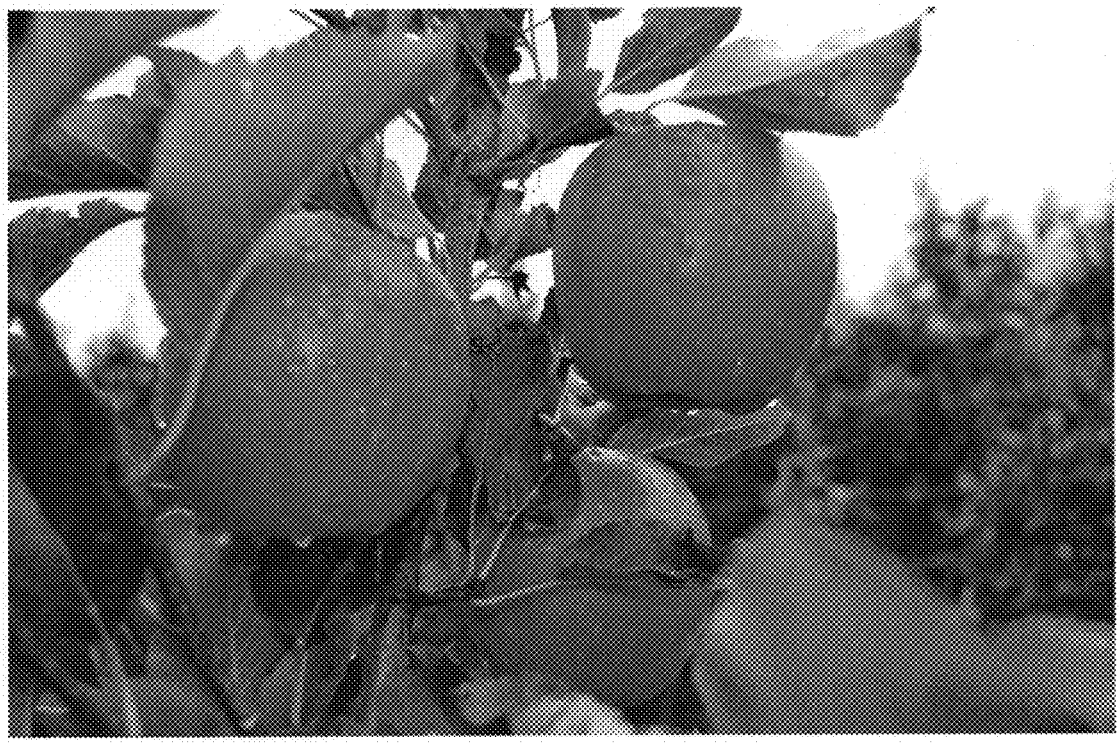
FIG. 4 is a close-up view of fruits of the new variety at maturity on the tree.

The following detailed description sets forth the characteristics of the new cultivar at approximately 3 years of age. The new variety was grown in an open field under standard apple orchard conditions in Neumarkt, Italy. The color readings were taken in natural daylight. Color references are primarily to The 2015 R.H.S. Colour Chart of The Royal Horticultural Society of London, Sixth Edition.

TREE

Age: Approximately 3 years.
Height: 2.8 m.
Width: 1.2 m.
Density: Medium.
Vigor: Moderate.
Growth type: Ramified; spreading.
Production: Similar to 'Golden Delicious', with regular and very good crop yield.
Bearing: On spurs and shoots.
Trunk:
- *Diameter.*—5.0 cm, measured at 3.0 cm above the grafting point.
- *Surface texture.*—Smooth, with prominent lenticels.
- *Bark color.*—165B.
- *Lenticels.*—Length: 1.0-3.0 mm. Width: 1.0-2.0 mm. Color: 156D. Density: Medium.

Branches:
*Form*.—Ramified.
*Diameter*.—12.0 mm for lower trunk branches.
*Color*.—177B.
*Surface texture*.—Smooth.
*Average angle*.—45-90°.
*Bud presence*.—On medium-long spurs and one-year old shoots.
*Lenticels*.—Length: 1.0-2.0 mm. Width: 1.0-2.0 mm. Shape: Oval to star form; irregular. Density: 5 to 10. Color: NN155D.

Leaves:
*Length*.—8.5 cm.
*Width*.—5.0 cm.
*Shape*.—Oval.
*Apex*.—Acuminate.
*Base*.—Equilateral and oblique.
*Margin*.—Serrate.
*Texture*.—Smooth.
*Thickness*.—Medium.
*Pubescence*.—Upper surface: Absent. Lower surface: Weak.
*Color*.—Young leaves: Upper surface: 141B, with red veins present. Lower surface: 141C, with red veins present. Mature leaves: Upper surface: 137A. Lower surface: 137B.
*Petiole*.—Shape: Orbicular. Length: 2.0-3.0 cm. Diameter: 2.0-3.0 cm. Color: Internally 147B, with some anthocyanin coloration present.
*Veins*.—Presence: Medium dense, intensified at the base. Color: Upper surface: 178B. Lower surface: 148C.

FLOWERS

Blooming time: Early to medium, depending on location.
Blooming period: Average.
Number of flowers per cluster: 5.
Pollination requirements: Normal, similar to 'Golden Delicious' and 'Granny Smith'.
Fragrance: Normal and medium.

Buds:
*Length*.—10.0-12.0 mm.
*Width*.—10.0-12.0 mm.
*Color*.—75A.

Pedicels:
*Length*.—22.0-25.0 mm.
*Diameter*.—1.0-1.5 mm.
*Color*.—143C.

Petals:
*Number per flower*.—5.
*Arrangement*.—Partially overlapping.
*Length*.—20.0 mm.
*Width*.—20.0 mm.
*Shape*.—Orbicular.
*Margin*.—Smooth; entirely cupped.
*Texture and appearance*.—Smooth (both surfaces).
*Color*.—When opening: Upper surface: 76D. Lower surface: 77D. Fully opened: Upper surface: Mostly 155D, with a touch of purple. Lower surface: Mostly 155D, with a touch of 76C.

Sepals:
*Length*.—5.0-7.0 mm.
*Width*.—3.0-4.0 mm.
*Shape*.—Pointed.
*Margin*.—Entire.
*Texture*.—Smooth (both surfaces).
*Upper surface color*.—144B.
*Lower surface color*.—144B.

Stamens:
*Number (per flower)*.—20-25.
*Filament length*.—5.0-15.0 mm.

Anthers:
*Shape*.—Elongated.
*Length*.—2.0 mm.
*Color*.—10B.

Pollen:
*Amount*.—Medium to high.
*Color*.—10B.

Pistils:
*Length*.—15.0-20.0 mm.

Style:
*Length*.—14.0-20.0 mm.
*Color*.—145D.

Stigma:
*Shape*.—Round.
*Color*.—11C.

FRUIT

Fruit:
*Average maturity/picking date*.—Late September in Italy.
*Average weight per fruit*.—210 g.
*Average fruit productivity per tree*.—High; 25-30 kg when grafted on M9 rootstock.
*Form*.—Elongated.
*Size*.—Axial diameter: 80.0-90.0 mm. Transverse diameter: 75.0-85.0 mm.
*Cavity*.—Shape: Tight. Depth: Average of 20.0 mm. Breadth: Average of 20.0 mm.
*Basin*.—Depth: 15.0 mm. Width: 25.0-30.0 mm.
*Calyx*.—Closed.

Skin:
*Thickness*.—Medium.
*Texture*.—Smooth.
*Tendency to crack*.—No.
*Color*.—46C.
*Ground color*.—17D.
*Lenticel number*.—High.

Flesh:
*Aroma*.—Fruity, very sweet, and aromatic.
*Color*.—155B.
*Texture*.—Crunchy.
*Eating quality*.—Very good; sweet.

Core:
*Bundle area*.—Compact and closed with small bundles.
*Capillary area*.—Small and closed.
*Calyx tube*.—Closed; 20.0-30.0 mm from tube to shoulder.
*Styles*.—Present.
*Stamens*.—Present.
*Stalk cavity*.—Depth: 15.0-20.0 mm. Breadth: 35.0 mm.
*Seed cells*.—Wall: Small and tight. Depth: 15.0 mm. Breadth: 5.0 mm. Longitudinal section: 20.0 mm.

Seeds:
*Number perfect*.—8-10.
*Number in one cell*.—2.
*Length*.—10.0 mm.

*Breadth.*—5.0 mm.

*Form.*—Elongated and flat.

*Color.*—175D.

Stem:

*Length.*—20.0-30.0 mm.

*Width.*—10.0-20.0 mm.

*Color.*—153B, with a touch of red.

Use: Table and dessert fruit for conventional and organic growing.

Shipping quality: Very good.

Keeping quality: Very good.

Tree winter hardiness: No frost damage; leaves fall in winter months.

Bud winter hardiness: No frost damage.

Drought tolerance: Similar to 'Gala'.

Disease resistance: None observed to date.

I claim:

1. A new and distinct variety of apple tree named 'Fengapi' as shown and described herein.

* * * * *